(12) United States Patent
Furuyashiki et al.

(10) Patent No.: US 10,286,005 B2
(45) Date of Patent: *May 14, 2019

(54) ANTIOXIDANT AGENT, AND ANTIOXIDANT COSMETIC AND UV CARE COSMETIC

(71) Applicant: EZAKI GLICO CO., LTD., Osaka-shi, Osaka (JP)

(72) Inventors: Takashi Furuyashiki, Osaka (JP); Hitoshi Ashida, Kobe (JP); Takakazu Mitani, Kobe (JP); Yasukiyo Yoshioka, Kobe (JP)

(73) Assignee: EZAKI GLICO CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/542,397

(22) PCT Filed: Jan. 4, 2016

(86) PCT No.: PCT/JP2016/050042
§ 371 (c)(1),
(2) Date: Jul. 7, 2017

(87) PCT Pub. No.: WO2016/111265
PCT Pub. Date: Jul. 14, 2016

(65) Prior Publication Data
US 2018/0000856 A1 Jan. 4, 2018

(30) Foreign Application Priority Data
Jan. 8, 2015 (JP) ................................. 2015-001966

(51) Int. Cl.
*A61K 31/715* (2006.01)
*A61K 8/73* (2006.01)
*A61K 9/00* (2006.01)
*A61Q 17/04* (2006.01)
*A61Q 19/00* (2006.01)
*A61K 31/716* (2006.01)

(52) U.S. Cl.
CPC .............. *A61K 31/715* (2013.01); *A61K 8/73* (2013.01); *A61K 9/0095* (2013.01); *A61K 31/716* (2013.01); *A61Q 17/04* (2013.01); *A61Q 19/00* (2013.01)

(58) Field of Classification Search
CPC ...... A61K 31/715; A61K 8/73; A61K 9/0095; A61Q 19/00; A61Q 17/04
USPC ............................................. 435/183; 514/54
See application file for complete search history.

(56) References Cited

U.S. PATENT DOCUMENTS

| | | | |
|---|---|---|---|
| 6,284,243 B1 | 9/2001 | Masuyama et al. | |
| 7,670,812 B2 * | 3/2010 | Kajiura | C12N 9/2411 435/101 |
| 8,461,130 B2 * | 6/2013 | Furuyashiki | A21D 2/181 514/54 |
| 2007/0248705 A1 | 10/2007 | Shimura et al. | |
| 2008/0131941 A1 | 6/2008 | Kajiura et al. | |
| 2010/0063000 A1 | 3/2010 | Furuyashiki et al. | |

FOREIGN PATENT DOCUMENTS

| | | |
|---|---|---|
| EP | 0 993 822 A1 | 4/2000 |
| JP | H01-279827 A | 11/1989 |
| JP | H07-102252 A | 4/1995 |
| JP | H08-073350 A | 3/1996 |
| JP | H09-023848 A | 1/1997 |
| JP | 2002-322078 A | 11/2002 |
| JP | 2002-370998 A | 12/2002 |
| JP | 2003-321373 A | 11/2003 |
| JP | 2003-335628 A | 11/2003 |
| JP | 2004-026766 A | 1/2004 |
| JP | 2007-031315 A | 2/2007 |
| JP | 2007-126455 A | 5/2007 |
| JP | 2009-227632 A | 10/2009 |
| JP | 2011-256126 A | 12/2011 |
| JP | 2013-510076 A | 3/2013 |
| JP | 2013-075917 A | 4/2013 |
| JP | 2013-126965 A | 6/2013 |
| WO | WO 2006/035848 A1 | 4/2006 |
| WO | WO 2006/043671 A1 | 4/2006 |
| WO | WO 2011/031304 A2 | 3/2011 |
| WO | WO 2012/035770 A1 | 3/2012 |

OTHER PUBLICATIONS

Glossary of medical education terms, Institute of International Medical Education. http://www.iime.org/glossary.htm Accessed in Mar. 2013. (Year: 2013).*

Tafazoli et al. Safety evaluation of an enzymatically-synthesized glycogen (ESG). Regulatory Toxicology and Pharmacology 57 (2010) 210-219. (Year: 2010).*

Itoh et al., "Reduced scytonemin isolated from *Nostoc commune* suppresses LPS/IFNγ-induced NO production in murine macrophage RAW264 cells by inducing hemeoxygenase-1 expression via the Nrf2/ARE pathway," *Food and Chemical Toxicology*, 69: 330-338 (2014).

Park et al., "TOP 1 and 2, polysaccharides from *Taraxacum officinale*, inhibit NFκB-mediated inflammation and accelerate Nrf2-induced antioxidative potential through the modulation of PI3K-Akt signaling pathway in RAW 264.7 cells," *Food and Chemical Toxicology*, 66: 56-64 (2014).

(Continued)

*Primary Examiner* — Yih-Horng Shiao
(74) *Attorney, Agent, or Firm* — Leydig, Voit & Mayer, Ltd.

(57) ABSTRACT

The present invention provides an antioxidant, an ROS inhibitor, an antioxidant enzyme production promoter, an antioxidant cosmetic, a UV care cosmetic, a prophylactic or therapeutic agent for gastrointestinal tract inflammation, and an antioxidant food or beverage, each containing an enzymatically synthesized glycogen (ESG) or an α-amylase digest (RG) thereof, as well as use for enhancing an antioxidative effect in vivo.

14 Claims, 12 Drawing Sheets

(56) References Cited

OTHER PUBLICATIONS

Qu et al., "The protective effect of magnesium lithospermate B against glucose-induced intracellular oxidative damage," *Biochemical and Biophysical Research Communication*, 411: 32-39 (2011).
Japanese Patent Office; International Search Report in International Patent Application No. PCT/JP2016/050042 (dated Mar. 22, 2016).
Kakutani et al., "The effect of orally administered glycogen on anti-tumor activity and natural killer cell activity in mice," *International Immunopharmacology*, 12(1): 80-87 (2012).
European Patent Office, Extended European Search Report in European Patent Application No. 16735004.0 (dated Nov. 22, 2018).

\* cited by examiner

Fig. 4
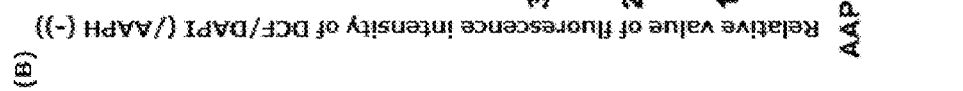
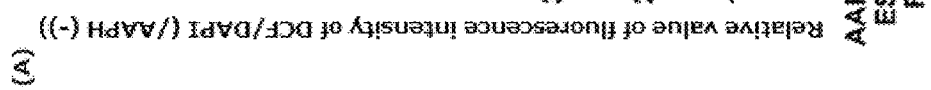

Fig. 7
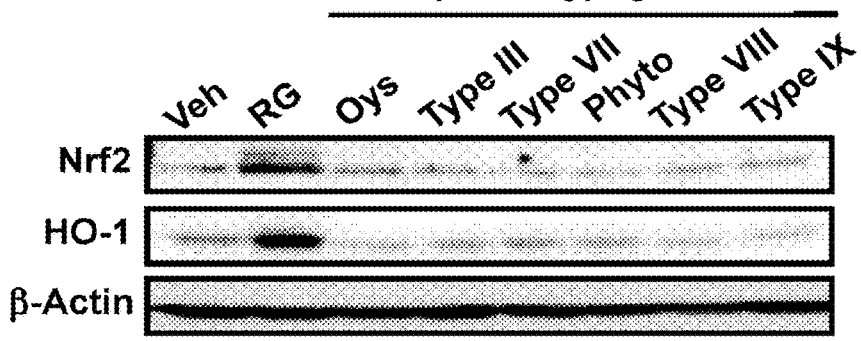
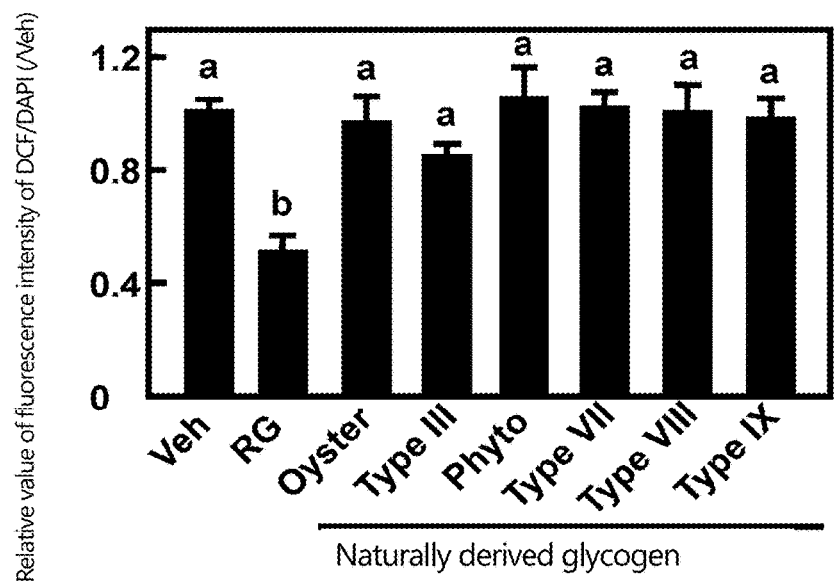

ANTIOXIDANT AGENT, AND ANTIOXIDANT COSMETIC AND UV CARE COSMETIC

CROSS-REFERENCE TO RELATED APPLICATIONS

This patent application is the U.S. national phase of International Patent Application No. PCT/JP2016/050042, filed on Jan. 4, 2016, which claims the benefit of Japanese Patent Application No. 2015-001966, filed Jan. 8, 2015, the disclosures of which are incorporated herein by reference in their entireties for all purposes.

TECHNICAL FIELD

The present invention relates to an antioxidant, an antioxidant cosmetic, or a UV care cosmetic. The present invention further relates to reactive oxygen spices inhibitor, an antioxidant enzymes production promoter, or a prophylactic or therapeutic agent for gastrointestinal inflammation.

Further, the present invention relates to an antioxidant food or beverage, and use for enhancing an antioxidative effect in vivo.

BACKGROUND ART

Intake of a component with a high antioxidative effect, such as vitamins, polyphenols, and carotenoids, is a usual method for increasing antioxidative capacity in vivo. In recent years, a technique has been developed for enhancing antioxidative capacity in vivo by increasing the amount of an antioxidant enzyme produced in vivo. For example, the following methods have been proposed for this purpose: a method for treating immune system cells with Western dandelion-derived polysaccharide (Non-patent Literature (NPL) 1); a method for treating immune system cells with Nostoc commune-derived scytonemin (NPL 2); and a method for eating an isohumulone or an isomerized hop extract (Patent Literature (PTL) 1). Natural products may be extremely expensive and the effects achieved by natural products may vary depending on the production lot (PTL 2 to PTL 5). Further, such natural products are generally unstable under light or heat. When natural products are incorporated into foods or beverages and used, a stability problem arises. Further, natural products are poorly soluble in water and are thus difficult to use for beverages, etc., (PTL 6 to PTL 8). Furthermore, an extract of a natural product contains multiple compounds and the active principle of a natural product may not be clearly identified (PTL 1).

Glycogen is known as a reserve polysaccharide in animals. Glycogen is a highly-branched polymer in which many glucose molecules are polymerized by α-1,4 and 1,6 glycosidic linkages. Glycogen is mainly produced in the liver and skeletal muscles and functions as temporary storage of excess glucose.

Patent Literature (PTL) 9 discloses that enzymatically synthesized glycogen comprehensively improves the blood glucose level, visceral fat level, blood cholesterol level, neutral fat level, etc.

Further, Patent Literature (PTL) 10 discloses a method for producing enzymatically synthesized glycogen.

Further still, Patent Literature (PTL) 11 discloses an external preparation for the skin, comprising enzymatically synthesized glycogen. However, the antioxidative effect of enzymatically synthesized glycogen is not disclosed therein.

CITATION LIST

Patent Literature

PTL 1: WO2006/043671
PTL 2: JPH9-23848A
PTL 3: JP2002-3709798A
PTL 4: JPH8-73350A
PTL 5: JPH1-279827A
PTL 6: JP2007-126455A
PTL 7: JP2007-126455A
PTL 8: JP 2013-510076A
PTL 9: JP2013-75917A
PTL 10: WO2006/035848
PTL 11: JP2009-227632A

Non-Patent Literature

NPL 1: Food Chem Toxicol, Vol. 66, pages 56-64 (2014)
NPL 2: Food Chem Toxicol, Vol. 69, pages 330-338 (2014)

SUMMARY OF INVENTION

Technical Problem

An object of the present invention is to provide an antioxidant and an antioxidant cosmetic that are inexpensive and highly safe and stable, and whose active principle is clear.

Another object of the present invention is to provide reactive oxygen spices (ROS) inhibitor, antioxidant enzymes production promoter, and a prophylactic or therapeutic agent for gastrointestinal inflammation.

A further object of the present invention is to provide a food or beverage having an antioxidative effect, as well as use for enhancing an antioxidative effect in vivo, such as in mammals.

Solution to Problem

The present inventors found that enzymatically synthesized glycogen (ESG) or an α-amylase digest of ESG (RG) has an antioxidative effect and a prophylactic or therapeutic effect for intestinal inflammation, and is also useful as a component of antioxidant and/or UV-care cosmetics, which alleviates damage to the skin due to oxidative stress and UV (UV-A, UV-B) irradiation, and as a component of antioxidant foods or beverages.

The present invention provides the following antioxidants, ROS inhibitors, antioxidant enzyme production promoters, antioxidant and/or UV-care cosmetics, prophylactic or therapeutic agents for gastrointestinal inflammation, antioxidant foods and beverages, and use for enhancing an antioxidative effect in vivo.

Item 1. An antioxidant comprising an enzymatically synthesized glycogen (ESG) or an α-amylase digest thereof (RG).
Item 2. An ROS inhibitor comprising an enzymatically synthesized glycogen (ESG) or an α-amylase digest thereof (RG).
Item 3. An antioxidant enzyme production promoter comprising an enzymatically synthesized glycogen (ESG) or an α-amylase digest thereof (RG).
Item 4. The production promoter according to Item 3, wherein the antioxidant enzyme is HO-1.
Item 5. The production promoter according to Item 3, wherein the antioxidant enzyme is NQO-1.

Item 6. The production promoter according to any one of Items 3 to 5, wherein the production of the antioxidant enzyme is promoted by increasing the expression of Nrf-2.

Item 7. An antioxidant cosmetic comprising an enzymatically synthesized glycogen (ESG) or an α-amylase digest thereof (RG).

Item 8. The antioxidant cosmetic according to Item 7, which exerts an antioxidative effect by promoting the production of an antioxidant enzyme.

Item 9. A UV care cosmetic comprising an enzymatically synthesized glycogen (ESG) or an α-amylase digest thereof (RG).

Item 10. A prophylactic or therapeutic agent for gastrointestinal inflammation, comprising an enzymatically synthesized glycogen (ESG) or an α-amylase digest thereof (RG).

Item 11. An antioxidant food or beverage comprising an enzymatically synthesized glycogen (ESG) or an α-amylase digest thereof (RG).

Item 12. Use of an enzymatically synthesized glycogen (ESG) or an α-amylase digest thereof (RG) for enhancing an antioxidative effect in vivo.

Advantageous Effects of Invention

According to the present invention, intestinal inflammation or oxidative stress to the skin due to UV irradiation or ROS can be alleviated by enhancing antioxidative capacity in vivo. The antioxidative effects, UV-care effects, and like effects of ESG, RG, etc., are considered to be based on inducing the expression of an antioxidant protein. These effects are effective in cells or in vivo.

According to the present invention, an enzymatically synthesized glycogen (ESG) or an α-amylase digest (RG) thereof that are highly safe and stable and whose active principle is clear can enhance antioxidative capacity in vivo or in the skin and prevent or treat skin trouble associated with oxidative stress and inflammation in the small intestine and large intestine.

The present invention is useful as a pharmaceutical composition, a food or beverage, a pharmaceutical preparation, and the like, that have antioxidative effects, active oxygen inhibitory effects, antioxidant enzyme production-promoting effects, and/or gastrointestinal inflammation-preventive effects.

BRIEF DESCRIPTION OF DRAWINGS

FIG. 1(A) shows the body weight. FIG. 1(B) shows the length of the large intestine (a photograph). FIG. 1(C) shows the length of the large intestine (a graph).

FIG. 4 shows the influence of ESG and RG on the accumulation of reactive oxygen species (ROS) in macrophage cells (RAW264.7).

FIG. 6(A) is a schematic diagram showing the relationship between RG (Enz), RG, and ESG. FIG. 6(B) shows the results of Western blot analysis of the expression levels of proteins involved in oxidative effects. FIG. 6(C) shows the ratio of DCF/DAPI. The graph shows relative values based on the vehicle (veh).

FIG. 7 shows the influence of naturally derived glycogen on the expression levels of antioxidant proteins and ROS accumulation (RAW264.7). FIG. 7(A) shows the results of Western blot analysis of the expression levels of proteins involved in antioxidative effects. FIG. 7(B) shows the results of calculating the DCF/DAPI ratio. The graph shows relative values based on the vehicle (veh).

FIG. 11(A) is a schematic diagram showing the relationship between ESG (Enz), RG (Enz), RG, and ESG. FIG. 11(B) shows the analytical results of ESG (Enz) and RG (Enz) in comparison with ESG and RG. FIG. 11(C) shows the results of calculation as a ratio of DCF/DAPI. The graph shows relative values based on UVB (+).

DESCRIPTION OF EMBODIMENTS

Figure 1:
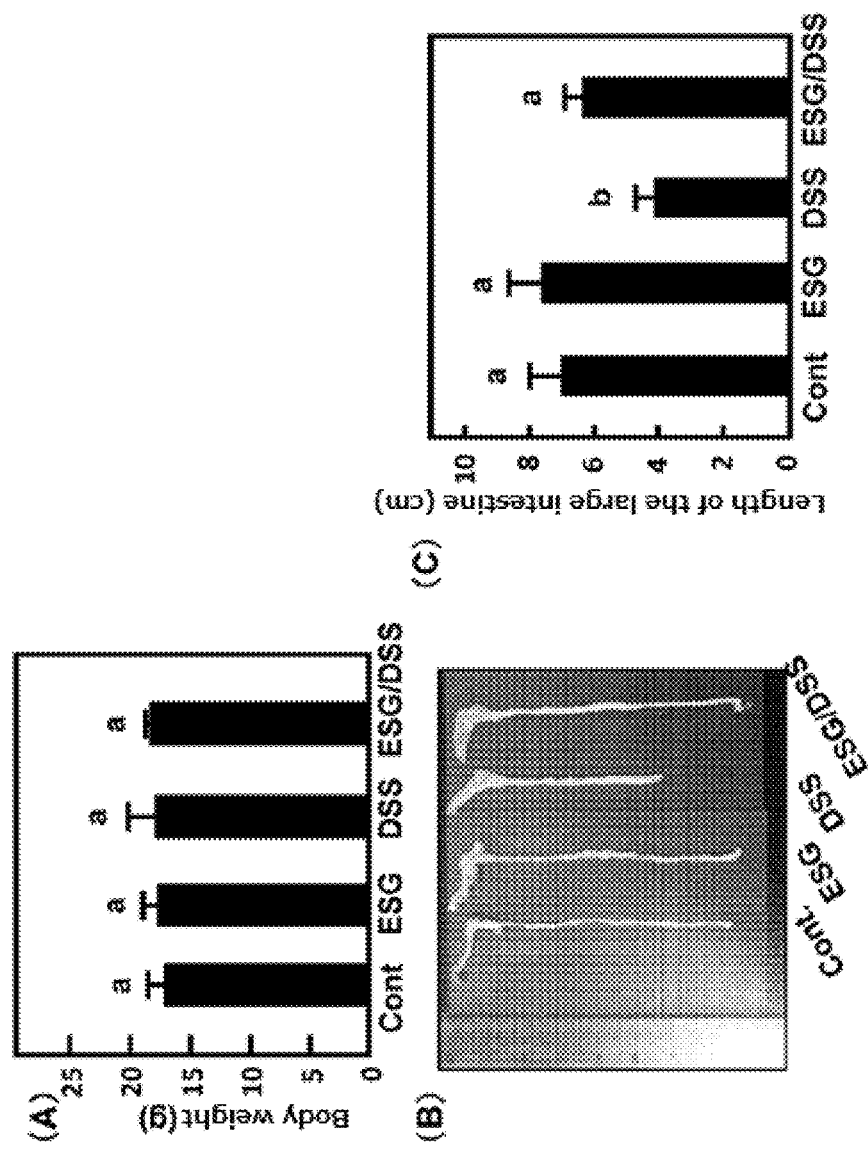
FIG. 1 shows the influence of ESG on shrinkage of the large intestine caused by dextran sulfate sodium (DSS) (in mice).

The enzymatically synthesized glycogen (ESG) used in the present invention may be, for example, one obtained in accordance with the method disclosed in Patent Literature (PTL) 10 (WO2006/035848). Specifically, the enzymatically synthesized glycogen (ESG) may be one produced by allowing a branching enzyme capable of synthesizing glycogen to act on a substrate in a solution to thereby produce glycogen. The substrate is an α-glucan linked mainly via α-1,4-glucoside bonds and having a degree of polymerization of 4 or more. A preferable substrate is, for example, debranched starch, debranched dextrin, or enzymatically synthesized amylose. A preferable enzymatically synthesized glycogen (ESG) has a weight average molecular weight of 1,000,000 Da or more; when the ESG is treated with 50 U/g substrate of pullulanase at 60° C. for 30 minutes, the resulting product has a weight average molecular weight of 500,000 Da or more as analyzed by the MALLS method; and when the ESG is treated with 300 U/g substrate of α-amylase of 37° C. for 30 minutes, the resulting product has a weight average molecular weight of 500,000 Da or more as analyzed by the MALLS method.

The digest (RG) obtained by digesting enzymatically synthesized glycogen (ESG) with α-amylase is a simulation of a product generated in the gastrointestinal tract of a mammal (e.g., a human) who digested ESG. In the Examples, RG prepared by digesting ESG with α-amylase in an amount of 400 U/g of ESG for 24 hours and then collecting an undigested high-molecular-weight fraction was used. ESG and RG are schematically shown in FIG. 6(A). Since natural glycogen does not exhibit antioxidant protein expression-inducing effects, antioxidative effects, UV care effects, etc., these effects are unique to ESG and RG. Examples of antioxidant enzymes include hemeoxygenase 1 (HO-1), NAD(P)H quinone oxidoreductase 1 (NQO1), and the like. Enzymatically synthesized glycogen (ESG) and an α-amylase digest thereof (RG) induces the expression of HO-1 and NQO-1, as well as Nrf2, which is a transcription factor involved in the expression of HO-1. One mechanism of the antioxidative effects of ESG and RG is inducing the expression of HO-1 and NQO-1 via Nrf2.

The second mechanism of antioxidative effects is the inhibition of a reactive oxygen species (ROS). The inhibition of ROS inhibits lipid oxidation, inflammation, etc., and inhibits cell damage by ROS. The antioxidant, ROS inhibitor, antioxidant enzyme production promoter, prophylactic or therapeutic agent for gastrointestinal inflammation of the present invention may be orally administered to exhibit antioxidative or like effects in vivo or may be applied to the skin as a cosmetic to produce such effects in the skin.

In the specification, "cosmetic" includes facial cosmetics, such as lotions, emulsions, creams, and packs; makeup cosmetics, such as foundations, lipsticks, and eye shadows; and the like. Examples of preferable uses of such cosmetics are antioxidation and UV care.

The present invention further provides foods or beverages containing ESG and/or RG.

In the present invention, examples of foods or beverages containing ESG or RG include milk beverages, fermented milk beverages, carbonated beverages, fruit-juice drinks, soft drinks, sports drinks, nutritional supplement beverages, candies, gums, chocolates, tablet confections, snacks, biscuits, jellies, jams, creams, baked confectioneries, ice creams, yogurts, butter, powdered milk, baked goods, supplements, nutritional dietary foods, liquid dietary foods, and the like. These foods and beverages preferably have antioxidative effects, ROS-inhibitory effects, antioxidant enzyme production-promoting effects, gastrointestinal tract inflammation-preventive effects, and the like.

ESG and/or RG exhibits antioxidative effects in vivo animals, in particular, mammals. Examples of mammals include humans, monkeys, cows, horses, pigs, goats, rabbits, rats, mice, hamsters, dogs, cats, and the like. Humans are particularly preferable. The antioxidant cosmetic and UV care cosmetic of the present invention may contain, in addition to enzymatically synthesized glycogen, at least one member selected from the group consisting of moisturizing components, skin-whitening components, ultraviolet absorbers/scattering agents, anti-inflammatory agents, cell activators, surfactants, antioxidants, and other components.

Examples of moisturizing components include ascorbic acid and derivatives thereof; vitamins other than ascorbic acid; pyridoxine derivatives, α-tocopherol derivatives, pantothenic acid derivatives; saccharides and saccharide derivatives, such as glucose, xylitol, and dextrin; D-panthenol and derivatives thereof; amino acids and derivatives thereof; polyhydric alcohols; phenol and derivatives thereof; collagens; mucopolysaccharides, such as hyaluronic acid; natural moisturizing factors, higher alcohols, lower alcohols, alcohols, mineral oils, vegetable fats and oils, animal fats and oils; hydroxycarboxylic acids and salts thereof; hydroxysalicylic acid glycosides, hydroxysalicylic acid aliphatic ester glycosides; hydroxycinnamic acid and derivatives thereof; caffeic acid and derivatives thereof; plant extracts, crude drug extracts, natural extracts, placenta extracts, oil-soluble licorice extracts, seaweed extracts, ceramides, ceramide analogues, crude sugar extracts, molasses extracts; mycelial cultures and extracts thereof; plant fermented extracts, yeast extracts, ferment extracts of various bacilli, urea, hinokitiol, sulfur; azelaic acid and azelaic derivatives; vitamin E-nicotinate and diisopropylamine dichloroacetate, deep sea water, alkaline simple hot spring water; phosphorylated saccharide and mineral salts thereof. These moisturizing components can be used singly or in a combination of two or more.

Examples of skin-whitening components include tyrosinase inhibitors, endothelin antagonists, α-MSH inhibitors, α-arbutin; arbutin and salts thereof, and derivatives thereof; ascorbic acid and derivatives thereof; ellagic acid compounds and alkali metal salts thereof; kojic acid and derivatives thereof; resorcinol derivatives, nordihydroguaiaretic acid, teprenone, allantoin, aminoethyl compounds, alkylenediamine carboxylic acid derivatives, betaine derivatives, acylmethyltaurines, hederacoside, gymnema saponins, beet saponins, γ-pyrrone glycosides, biphenyl compounds, sodium bisulfite, fibronectins, plant extracts, and the like. These skin-whitening components can be used singly or in a combination of two or more.

Examples of ultraviolet absorbers/scattering agents include benzoic acid-based ultraviolet absorbers such as paraaminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA amyl ester, and N,N-dimethyl PABA octyl ester; anthranilic acid-based ultraviolet absorbers such as homomenthyl-N-acetylanthranilate; salicylic acid-based ultraviolet absorbers such as amylsalicylate, menthylsalicylate, homomenthylsalicylate, octylsalicylate, phenylsalicylate, benzylsalicylate, and p-isopropanolphenylsalicylate; cinnamic acid-based ultraviolet absorbers, such as octylcinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl-p-methoxycinnamate(2-ethylhexyl-p-methoxycinnamate), 2-ethoxyethyl-p-methoxycinnamate, cyclohexyl-p-methoxycinnamate, ethyl-α-cyanophenylcinnamate, 2-ethylhexyl-α-cyano-β-phenylcinnamate, and glyceryl mono-2-ethylhaxanoyl-diparamethoxycinnamate; benzophenone-based ultraviolet absorbers, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, salts of 2-hydroxy-4-methoxybenzophenone-5-sulfonic acid, 4-phenyibenzophenone, 2-ethylhexyl-4'-phenyl-benzophenone-2-carboxylate, 2-hydroxy-4-n-octoxybenzophenone, and 4-hydroxy-3-carboxybenzophenone; and other ultraviolet absorbers such as 3-(4'-methylbenzylidene)-d,l-camphor, 3-benzylidene-d,l-camphor, urocanic acid, ethyl urocanate ester, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole, dibenzalazine, dianisoylmethane, 4-methoxy-4'-t-butyldibenzoylmethane, 5-(3,3-dimethyl-2-norbornylidene)-3-pentan-2-one), and zinc oxide; and the like. Such ultraviolet absorbers/scattering agents can be used singly or in a combination of two or more.

Examples of cell-activating agents include CoQ10; deoxyribonucleic acid and salts thereof; adenylic acid derivatives and salts thereof, such as adenosine triphosphate and adenosine monophosphate; ribonucleic acids and salts thereof; cyclic AMP, cyclic GMP, flavin adenine nucleotide, guanine, adenine, cytosine, thymine, xanthine, and their derivatives; caffeine; theophylline and salts thereof; retinal and retinol derivatives, such as retinol palmitate and retinol acetate; retinal and retinal derivatives, such as dehydroretinal; carotene and like carotenoids and A vitamins; resveratrol and resveratrol glycosides; thiamine and thiamine salts, such as thiamine hydrochloride and thiamine sulfate; riboflavin and riboflavin salts, such as riboflavin acetate; pyridoxine and pyridoxine salts, such as pyridoxine hydrochloride and pyridoxine dioctanoate; flavin adenine nucleotide; cyanocobalamin; folic acids; nicotinic acid and nicotinic acid derivatives, such as nicotinic acid amide and benzyl nicotinate; B vitamins, such as cholines; γ-linolenic acid and derivatives thereof; eicosapentaenoic acid and derivatives thereof; estradiol and derivatives thereof, and salts thereof; organic acids, such as glycolic acid, succinic acid, lactic acid, and salicylic acid, and derivatives thereof, and salts thereof; plant extracts, seaweed extracts, and the like. Such cell-activating agents can be used singly or in a combination of two or more.

Examples of antioxidants include A vitamins and derivatives thereof, and salts thereof, such as retinol, dehydroretinol, retinol acetate, retinol palmitate, retinal, retinoic acid, and vitamin A oil; carotenoids and derivatives thereof, such as α-carotene, β-carotene, γ-carotene, cryptoxanthin, astaxanthin, and fucoxanthin; B vitamins, derivatives thereof, and salts thereof, such as pyridoxine, pyridoxal, pyridoxal-5-phosphate ester, and pyridoxamine; C vitamins, derivatives thereof, and salts thereof, such as ascorbic acid, sodium ascorbate, ascorbyl stearate, ascorbyl palmitate, ascorbyl dipalmitate, and magnesium ascorbyl phosphate; D vitamins, derivatives thereof, and salts thereof, such as ergocalciferol, cholecalciferol, and 1,2,5-dihydroxy-cholecalciferol; E vitamins, derivatives thereof, and salts thereof, such as α-tocopherol, β-tocopherol, γ-tocopherol, δ-tocopherol, α-tocotrienol, β-tocotrienol, γ-tocotrienol, δ-tocotrienol, tocopherol acetate, and tocopherol nicotinate; trolox, derivatives thereof, and salts thereof; dihydroxytoluene, butylhydroxytoluene, butylhydroxyanisole, dibutylhydroxytoluene, α-lipoic acid, dehydrolipoic acid; glutathione, derivatives thereof, and salts thereof; uric acid; erythorbic acid, derivatives thereof, and salts thereof, such as erythorbic acid and sodium erythorbate; gallic acid, derivatives thereof, and salts thereof, such as gallic acid and propyl gallate; rutin, derivatives thereof, and salts thereof, such as rutin and α-glycosylrutin; tryptophan, derivatives thereof, and salts thereof; histidine, derivatives thereof, and salts thereof; cysteine derivatives and salts thereof, such as N-acetylcysteine, N-acetylhomocysteine, N-octanoylcysteine, and N-acetylcysteine methyl ester; cystine derivatives and salts thereof, such as N,N'-diacetylcystine dimethyl ester, N,N'-dioctanoylcystine dimethyl ester, and N,N'-dioctanoylhomocystine dimethyl ester; carnosine, derivatives thereof, and salts thereof; homocarnosine, derivatives thereof, and salts thereof; anserine, derivatives thereof, and salts thereof; carcinin, derivatives thereof, and salts thereof; histidine- and/or tryptophan- and/or histamine-containing dipeptide or tripeptide derivatives and salts thereof; flavonoids such as flavanone, flavone, anthocyanin, anthocyanidin, flavonol, quercetin, quercitrin, myricetin, fisetin, hamamelis tannin, catechin, epicatechin, gallocatechin, epigallocatechin, epicatechin gallate, and epigallocatechin gallate; tannic acid, caffeic acid, ferulic acid, protocatechuic acid, chalcone, oryzanol, carnosol, sesamol, sesarnine, sesamolin, gingerone, curcumin, tetrahydrocurcumin, clovamide, deoxyclovamide, shogaols, capsaicin, vanillylamide, ellagic acid, bromphenol, flavoglassine, melanoidin, riboflavin, riboflavin butyrate esters, flavin mononucleotide, flavin adenine nucleotide, ubiquinone, ubiquinol, mannitol, bilirubin, cholesterol, ebselene, selenomethionine, ceruloplasmin, transferrin, lactoferrin, albumin, bilirubin, superoxide dismutase, catalase, glutathione peroxidase, metallothionein, O-phosphono-pyridoxylidene rhodamine; N-(2-hydroxybenzyl)amino acid, derivatives thereof, and salts thereof, and N-(4-pyridoxylmethylene)amino acid, derivatives thereof, and salts thereof disclosed in U.S. Pat. No. 5,594,012; plant extracts, seaweed extracts; and the like. Such antioxidants can be used singly or in a combination of two or more.

Examples of surfactants include anionic surfactants such as fatty acid sodium salts, monoalkyl sulfate, alkyl polyoxyethylene sulfate, alkylbenzene sulfonate, and monoalkyl phosphate; cationic surfactants, such as alkyl trimethyl ammonium salts, dialkyl dimethyl ammonium salts, and alkylbenzyldimethyl ammonium salts; amphoteric surfactants, such as alkyl dimethyl amine oxide and alkyl carboxy betaine; and non-ionic surfactants, such as polyoxyethylene alkyl ether, sorbitan fatty acid ester, alkyl polyglucoside, fatty acid diethanolamide, and alkyl monoglyceryl ether; natural surfactants, such as lecithin; and the like. Such surfactants can be used singly or in a combination of two or more.

Examples of anti-inflammatory agents include zinc oxide; sulfur and derivatives thereof; glycyrrhizic acid and derivatives thereof, and salts thereof, such as glycyrrhizic acid, dipotassium glycyrrhizinate, and monoammonium glycyrrhizinate; glycyrrhetic acids and derivatives thereof, and salts thereof, such as β-glycyrrhetic acid, stearyl glycyrrhetinate, and disodium 3-succinyloxyglycyrrhetinate; tranexamic acid, chondroitin sulfuric acid, mefenamic acid, phenylbutazone, indomethacin, ibuprofen, ketoprofen, allantoin, guaiazulene, derivatives thereof, and salts thereof; extracts of various microorganisms, plants, and animals; and the like. Such anti-inflammatory agents can be used singly or in a combination of two or more.

Examples of other components include fragrances such as refined oils; colors such as pigments and synthetic dyes; blood circulation-enhancers; and the like. Such surfactants can be used singly or in a combination of two or more.

The "gastrointestinal tract inflammation" as used herein includes gastrointestinal tract diseases in which inflammation associated with ROS or oxidative stress occurs in a gastrointestinal tract, or symptoms of such an inflammation are exhibited. Specific examples include gastritis, colitis, hemorrhagic colitis, ulcerative colitis, anaphylactic enteritis syndrome, and the like. The prophylactic or therapeutic agent of the present invention can cure gastrointestinal tract inflammation or alleviate symptoms of the inflammation.

The amount of ESG or RG in the cosmetic of the present invention is not particularly limited as long as an antioxidative effect or UV care effect is exhibited. The amount may be, for example, about 0.01 to 10 mass %, and preferably about 0.05 to 5 mass %.

The amount of ESG or RG in the food or beverage of the present invention is not particularly limited as long as an antioxidative effect is exhibited. The amount may be, for example, about 0.01 to 50 mass %, and preferably about 0.05 to 20 mass %.

In the use for increasing the antioxidative effect in vivo according to the present invention, daily intake of ESG or RG per adult is about 0.1 to 20 g, and preferably about 1 to 10 g. Application of the antioxidant cosmetic or UV care cosmetic of the present invention to the skin ameliorates or alleviates damage due to oxidative stress or UV rays.

The daily dose per adult of the prophylactic or therapeutic agent for gastrointestinal inflammation of the present invention is about 0.1 to 20 g, and preferably about 1 to 10 g. The prophylactic or therapeutic agent can be administered once a day or in two to four divided doses per day. Daily intake of the prophylactic agent for gastrointestinal tract inflammation of the present invention in the form of a food or beverage, including supplements, can prevent or alleviate gastrointestinal tract inflammation.

EXAMPLES

The present invention is described in detail below with reference to Examples.

The ESG and RG used in the Examples were prepared and/or obtained in the following manner. Since about 20 mass % of ESG orally ingested by a mammal converts to RG (T. Furuyashiki et al., Food Funct., 2011, 2, 183-189), RG was administered in an amount corresponding to 20 mass % of ESG.

ESG was prepared in accordance with the method disclosed in Patent Literature (PTL) 10 (WO2006/035848). RG was prepared by using ESG as a substrate and treating ESG with α-amylase in an amount of 400 U/g of the substrate at 37° C. for 24 hours, followed by purification of an undigested high-molecular-weight fraction.

ESG (Enz) was prepared by using ESG as a substrate and treating ESG with a sufficient amount of α-amylase and isoamylase at 37° C. for 2 hours, followed by treatment with a sufficient amount of glucoamylase at 37° C. for 24 hours to completely digest ESG into glucose. After the enzymatic treatment, the amount of glucose was quantified to confirm complete decomposition.

RG (Enz) was prepared by using RG as a substrate and completely digesting RG into glucose by performing the same treatment as in the production of ESG (Enz). After the enzymatic treatment, the amount of glucose was quantified to confirm complete decomposition.

Example 1: Influence on Shrinkage of the Large Intestine Caused by DSS (FIG. 1)

As test animals, C57BL/6 mice (6-week-old, female) were purchased from Japan SLC. After one week of preliminary breeding, the mice were divided into four groups (A, B, C, D) and each group was subjected to the following treatments.
A) ESG (100 mg) dissolved in water was orally administered for two weeks. (ESG group)
B) ESG (100 mg) dissolved in water was orally administered for two weeks. One week after starting the administration, drinking water was changed to water containing 2% dextran sulfate sodium (DSS) (molecular weight: 36,000 to 50,000). This water was used continuously until the completion of breeding. (ESG/DSS group)
C) ESG-free water was orally administered for 2 weeks. (Control group)
D) ESG-free water was orally administered for 2 weeks. One week after starting the administration, drinking water was changed to water containing 2% DSS. This water was used continuously until the completion of breeding. (DSS group)

The breeding was performed according to a plan in compliance with "Kobe University, Roko-dai District, Animal Experiment Committee Regulations (approval number: 26-05-12) with the approval of the animal experiment committee. The breeding was performed in a room adjusted to the following conditions: room temperature: 25±2° C.; humidity as is; illuminated time period/day (9:00 to 21:00). The body weight was measured every day (FIG. 1(A)). After completion of the breeding, blood was collected from the heart under anesthesia and the large intestine was excised to measure the length of the large intestine (FIG. 1(B)). FIG. 1(A) and FIG. 1(C) show a significant difference (p<0.05) between the different alphabetical letters (a, b). The results in FIG. 1 clearly show that ESG can prevent or treat inflammation of the large intestine.

Figure 2:
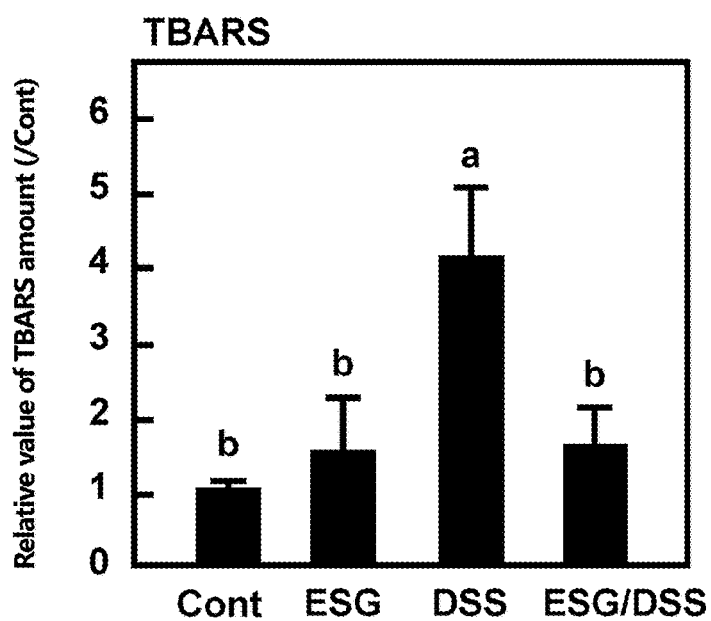
FIG. 2 shows the influence of ESG on accumulation of oxidative stress in large intestine tissue (in mice).

Example 2: Influence on Accumulation of Oxidative Stress in Large Intestine Tissue (FIG. 2)

As an index of oxidative stress in the large intestine, the amount of lipoperoxides was measured in terms of 2-thiobarbituric acid-reactive substances (TBARS), which are reaction products of lipoperoxides with 2-thiobarbituric acid. The large intestine tissue (30 mg) of mice collected in the experiment of Example 1 was finely cut with scissors. After 1 mL of a buffer (20 mM Hepes-NaOH, pH 7.5, containing 0.5% Nonidet P-40, 1 mM EDTA, 1 μM butylated hydroxytuluene, 1 mM phenylmethlsulfonyl fluoride, and 10 μg/ml leupeptin) was added, the resulting mixture was homogenized with a homogenizer and then centrifuged at 20,000×g and 4° C. for 20 minutes. The supernatant was collected as the total protein fraction. The protein fraction (150 μg/125 μL) was mixed with 20% trichloroacetic acid (75 μL) and 0.8% 2-thiobarbituric acid (50 μL). The mixture was incubated at 90° C. for 40 minutes. After cooling to room temperature, the fluorescence intensity (excitation/absorption: 530 nm/590 nm) of TBARS was measured. The graph in FIG. 2 shows relative values based on the control (Cont). The results of statistical analysis (ANOVA with post hoc Tuley) show a significant difference (p<0.05) between the different alphabetical letters (a, b). The results clearly show that ESG can significantly inhibit an increase of lipid peroxides and ROS induced by DSS.

Figure 3:
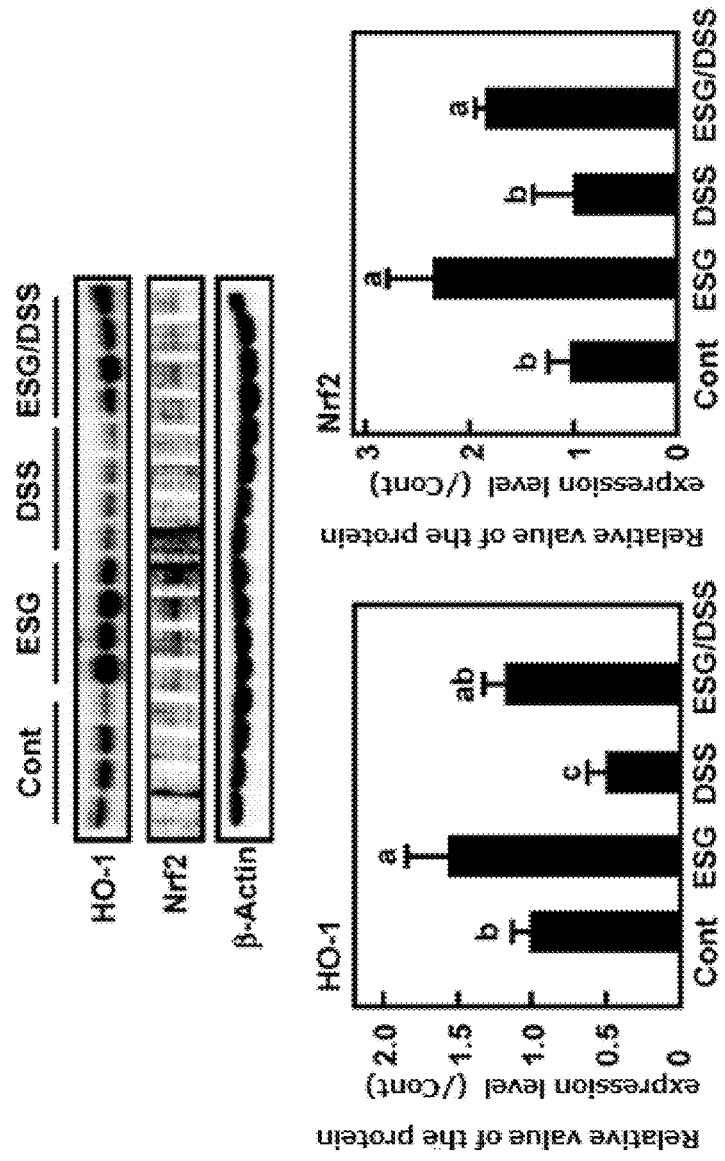
FIG. 3 shows the effects of ESG on the expression levels of antioxidant proteins in large intestine tissue (mice).

Example 3: Effect on the Expression Level of Antioxidant Protein in Large Intestine Tissue (FIG. 3)

The large intestine tissue (30 mg) collected in the experiment of Example 1 was finely cut with scissors. After 1 mL of a lysis buffer (50 mM Tris-HCl, pH 7.5, containing 150 mM NaCl, 0.5% Nonidet P-40, 10 mM sodium pyrophosphate, 2 mM EDTA, 1 mM phenylmethylsulfonyl fluoride, and 10 μg/mL leupeptin) was added, the resulting mixture was homogenized with a homogenizer and then centrifuged at 20,000×g and 4° C. for 20 minutes. The supernatant was collected as the total protein fraction. The collected protein was subjected to Western blotting to evaluate the expression levels of NF-E2 related factor 2 (Nrf2), heme oxygenase-1 (HO-1), and β-actin. The band strength of each protein obtained in Western blotting was quantified using an image analysis software (Image J) and normalized to the band strength of β-actin, which is a housekeeping gene. The graph shows relative values based on the control (Cont). The results of statistical analysis (ANOVA with post hoc Tukey) show a significant difference (p<0.05) between the different alphabetical letters (a, b, c). The results clearly show that ESG significantly increases the expression of HO-1 and Nrf2.

Example 4: Influence on the Accumulation of Reactive Oxygen Species (ROS) in Cultured Cells (FIG. 4)

Many large macrophage cells are present in large intestinal epithelium, and stimulation of microphage cells by oxidative stress leads to secretion of inflammatory cytokines. Further, inflammatory cytokines are considered to cause oxidative stress and thereby induce a negative cycle, thus leading to colitis. Accordingly, the effect of ESG on the accumulation of oxidative stress in macrophage cells was investigated.

Mouse macrophage cells (RAW264.7 cells) were purchased from American Type Culture Collection (Manassas, Va., USA). The cells were cultured in a medium (DIEM-HG) prepared by adding D-glucose at a final concentration of 4.5 g/L to Dulbecco's modified Eagle's medium containing 10% fetal bovine serum. ESG or RG was added to the medium in which RAW264.7 cells were cultured, and ESG or RG was allowed to act for 24 hours. Then, after the medium was replaced with a fresh DMEM-HG medium, an ROS generator 2,2'-azobis(2-methylpropionamidine)dihydrochloride (AAPH) was added to the medium to a final concentration of 4 mM, and the cells were cultured. One hour after the addition of AAPH, an ROS detection reagent (dichlorodihydrofluorescein diacetate (DCF-DA), (20 μM)) was added to the medium, and the cells were further cultured for 30 minutes. After completion of the culture, the cells were washed and the nuclei were stained with 4',6-diamidino-2-phenylindole (DAPI). The fluorescence intensity of DCF and DAPI was measured at 485 nm/535 nm and 355 nm/380 nm and calculated as a ratio of DCF/DAPI. The graphs in FIG. 4(A) and FIG. 4(B) show the relative values based on AAPH (-). The results of statistical analysis (ANOVA with post hoc Tukey) show a significant difference ($p<0.05$) between the different alphabetical letters (a, b, c, d, e). The results in FIG. 4 clearly show that RG reduces the ROS amount in a concentration-dependent manner. Since 20 mass % of ESG converts to ESG in the gastrointestinal tract, ESG also similarly reduces the ROS amount in a concentration-dependent manner.

Figure 5:
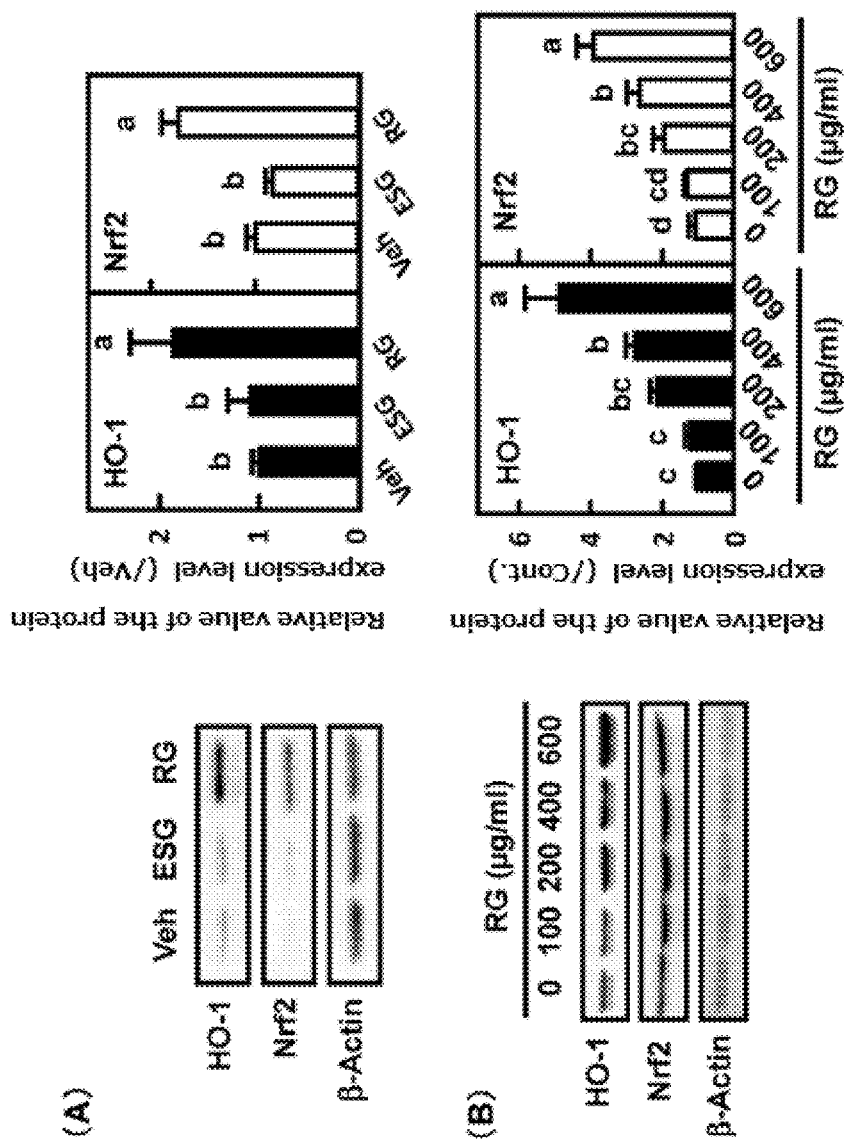
FIG. 5 shows the effects of ESG and RG on the expression levels of antioxidant proteins in macrophage cells (RAW264.7).

Example 5: Effects on the Expression Level of Antioxidant Protein in Macrophage Cells (FIG. 5)

The mouse macrophage cells (RAW264.7 cells) were purchased from American Type Culture Collection (Manassas, Va., USA). The cells were cultured in a medium (DMEM-HG) prepared by adding D-glucose at a final concentration of 4.5 g/L to Dulbecco's modified Eagle's medium containing 10% fetal bovine serum.

(A) ESG and RG were added to a final concentration of 400 μg/mL to a medium in which RAW264.7 cells were cultured, and ESG and RG were allowed to act for 24 hours.

(B) RG was added to a final concentration of 0 to 600 μg/mL to a medium in which RAW264.7 cells were cultured, and RG was allowed to act for 24 hours.

The cells were then collected. The expression level of each protein involved in antioxidative effects was analyzed by Western blotting. The band strength of each protein obtained by Western blotting was calculated using an image analysis software (Image J) and normalized to the band strength of β-actin, which is a housekeeping gene. The graphs in FIG. 5(A) and FIG. 5(B) show relative values based on the control (Cant). The results of statistical analysis (ANOVA with post hoc Tukey) show a significant difference ($p<0.05$) between the different alphabetical letters (a, b, c, d). The results clearly show that RG promotes the expression of an antioxidant protein (HO-1) and its transcription factor Nrf2 in a concentration-dependent manner. ESG promotes the expression of an antioxidant protein (HO-1) and its transcription factor Nrf2 in a concentration-dependent manner via RG produced in the gastrointestinal tract of a mammal.

Figure 6:
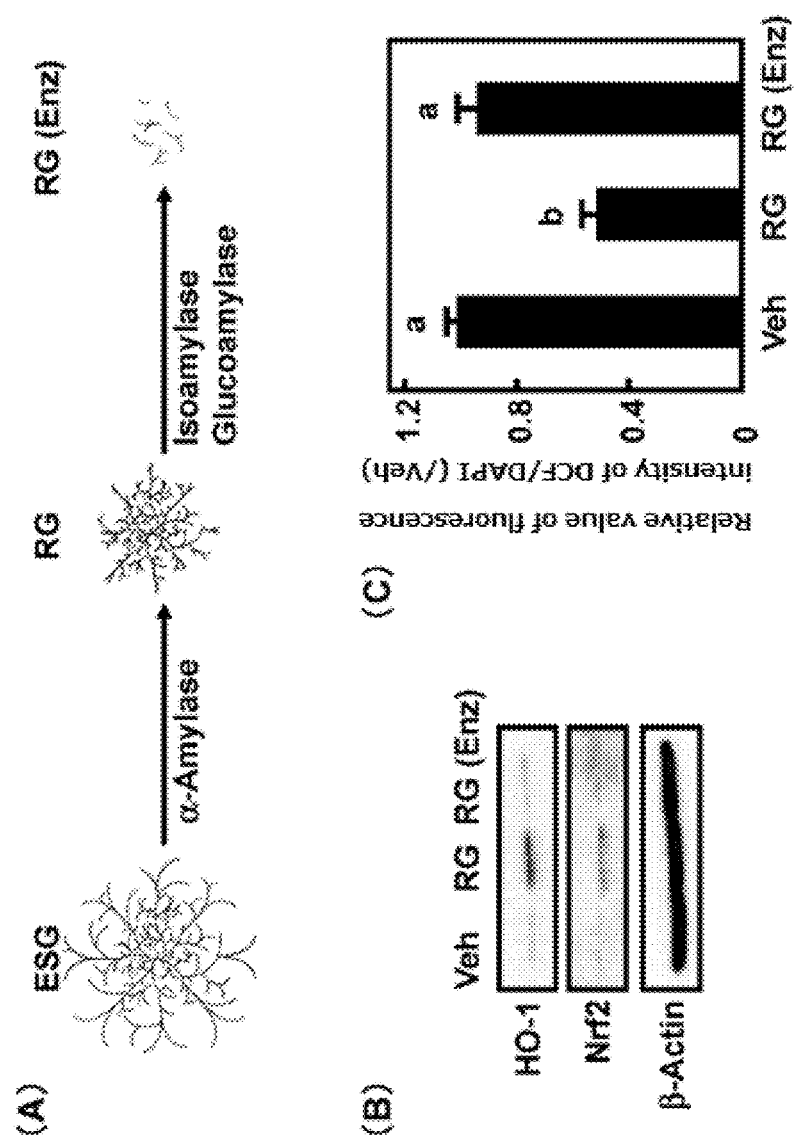
FIG. 6 shows the effects of ESG and RG on the expression levels of antioxidant proteins in macrophage cells (RAW264.7).

Example 6: Effect on the Expression Level of Antioxidant Protein in Macrophage Cells (FIG. 6)

To investigate whether an increase in the expression level of an antioxidant protein by RG is induced in an RG-structure-specific manner, RG (Enz), which is a product obtained by digesting RG with isoamylase and glucoamylase into glucose, was analyzed in comparison with RG (FIG. 6(A)).

ESG or RG or RG (Enz) was added to a final concentration of 400 μg/mL to medium in which RAW264.7 cells were cultured, and each was allowed to act on the cells for 24 hours. The cells were then collected, and the expression levels of the protein involved in antioxidative action were analyzed by Western blotting (FIG. 6(B)).

ESG or RG or RG (Enz) was added to a final concentration of 400 μg/mL to medium in which RAW264.7 cells were cultured, and each was allowed to act on the cells for 24 hours. The medium was then replaced with a fresh DMEM-HG medium. As an ROS generator, 2,2'-Azobis(2-methylpropionamidine)dihydrochloride (AAPH) was added to the medium to a final concentration of 4 mM, and the cells were cultured. As an ROS detection reagent, dichlorodihydrofluorescin diacetate (DCF-DA) (20 μM) was added to the medium 1 hour after the addition of AAPH. The cells were further cultured for 30 minutes. After completion of the culture, the cells were washed and the nuclei were stained with 4',6-diamidino-2-phenylindole (DAPI). The fluorescence intensity of DCF and DAPI was measured at 485 nm/535 nm and 355 nm/380 nm, and calculated as a ratio of DCF/DAPI (FIG. 6(C)). The graph in FIG. 6(C) shows relative values based on veh (only the solvent). The results of statistical analysis (ANOVA with post hoc Tukey) show a significant difference ($p<0.05$) between the different alphabetical letters (a, b). The results in FIG. 6 clearly show that enzymatically decomposed RG (Enz) has no effect and it is RG that promotes the expression of an antioxidant protein (HO-1) and its transcription factor Nrf2 in a concentration-dependent manner.

Example 7: Influence on the Expression Level of Antioxidant Protein and Accumulation of ROS (FIG. 7)

(A) Each of six kinds of naturally derived Glycogens (oyster/Oys, rabbit/Type III, muscle/Type VII, sweet corn/Phyto, slipper limpet/Type VIII, bovine liver/Type IX) or RG was added to a final concentration of 400 μg/mL to medium in which RAW264.7 cells were cultured, and each was allowed to act on the cells for 24 hours. The cells were then collected. The expression levels of proteins involved in antioxidative effects were analyzed by Western blotting (FIG. 7(A)).

(B) Each of six kinds of naturally derived glycogens (oyster/Oys, rabbit/Type III, muscle/Type VII, sweet corn/Phyto, slipper limpet/Type VIII, bovine liver/Type IX) or RG was added to a final concentration of 400 μg/mL to medium in which RAW264.7 cells were cultured, and each was allowed to act for 24 hours. The medium was then replaced with a fresh DMEM-HG medium. As an ROS generator, 2,2'-azobis(2-methylpropionamidine)dihydrochloride (AAPH) was added to the medium to a final concentration of 4 mM, and the cells were cultured. As an ROS detection reagent, dichlorodihydrofluorescin diacetate (DCF-DA) (20 μM) was added to the medium 1 hour after the addition of AAPH. The cells were further cultured for 30 minutes. After completion of the culture, the cells were washed and the nuclei were stained with 4',6-diamidino-2-phenylindole (DAPI). The fluorescence intensity of DCF and DAPI was measured at 485 nm/535 nm and 355 nm/380 nm and calculated as a ratio of DCF/DAPI (FIG. 7(B)). The graphs in FIG. 7(A) and FIG. 7(B) show relative values based on veh. The results of statistical analysis (ANOVA with post hoc Tukey) show a significant difference ($p<0.05$) between the different alphabetical letters (a, b).

Example 8: Influence on the Expression Level of Antioxidant Protein in NHEK (FIG. 8)

Normal human epidermal keratinocytes (NHEK) were purchased from Kurabo Industries, Ltd. (Osaka, Japan). The cells were cultured in EpiLife® medium in the presence of 5% $CO_2$ at 37° C.

ESG, RG, and oyster-derived glycogen were added to the medium to a final concentration of 300 or 600 µg/mL and allowed to act for 24 hours. The cells were then collected. The expression levels of proteins involved in antioxidative effects (Nrf2, HO-1, and NQO-1) were analyzed by Western blotting (FIG. 8(A)).

Figure 8:
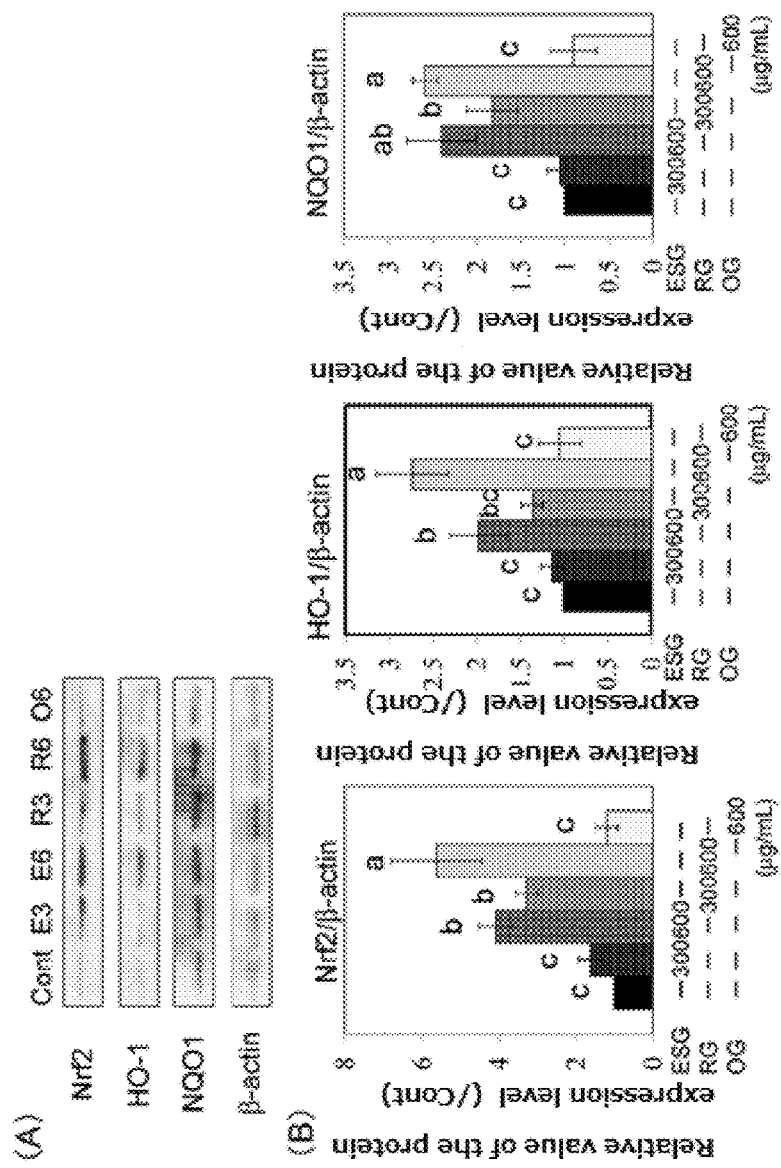
FIG. 8 shows the influence of ESG and RG on the expression levels of antioxidant proteins in normal human epidermal keratinocytes (NHEK).

The band strength of each protein obtained by Western blotting was quantified using an image analysis software (Image J) and standardized to the band strength of β-actin (FIG. 8(B), FIG. 8(C), FIG. 8(D)). The graphs in FIG. 8 show relative values based on UVB-. The results of statistical analysis (ANOVA with post hoc Tukey) show a significant difference ($p<0.05$) between the different alphabetical letters (a, b, c). The results in FIG. 8 clearly show that ESG and RG both promote the production of Nrf2, HO-1, and NQO-1 in a concentration-dependent manner.

Figure 9:
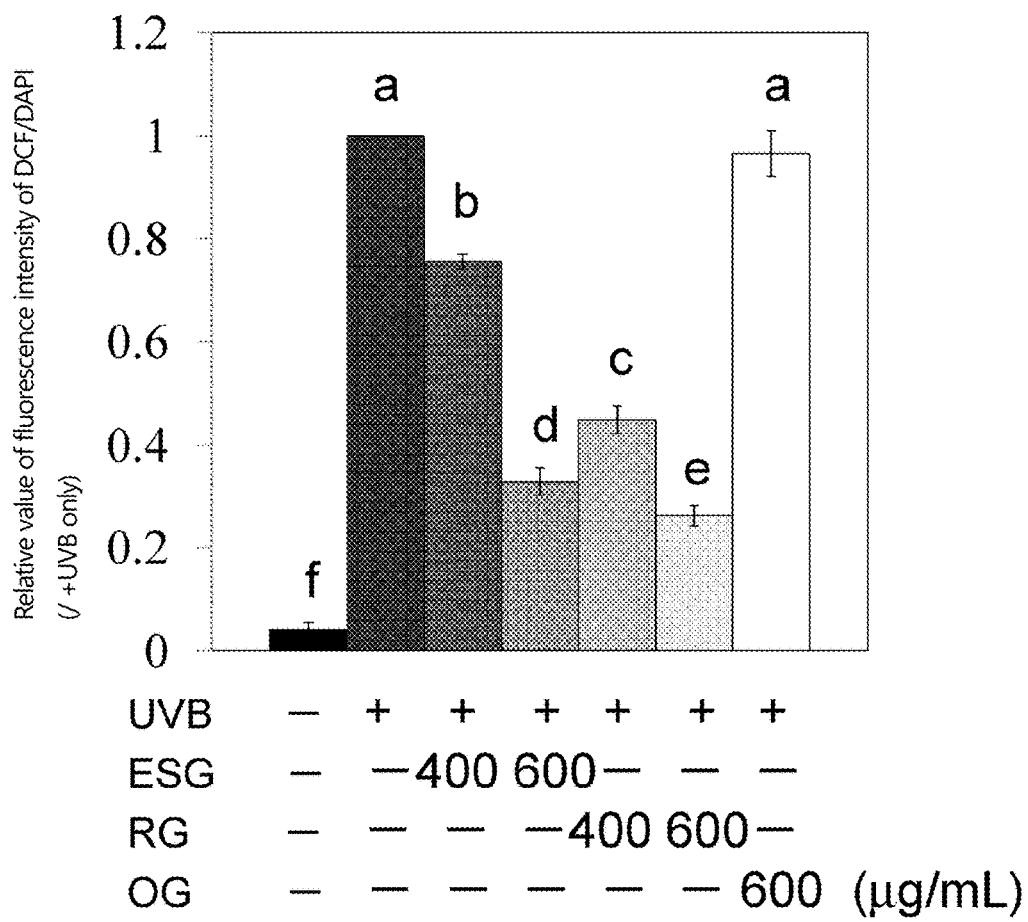
FIG. 9 shows the influence of ESG and RG on UVB irradiation-induced ROS accumulation in NHEK.

Example 9: Influence on UVB Irradiation-Induced ROS Accumulation in NHEK (FIG. 9)

NHEK was seeded in 35-mm dishes. ESG, RG, and oyster-derived glycogen (OG) were added to a final concentration of 400 or 600 µg/mL, and were allowed to act for 24 hours. After UVB irradiation (20 $mJ/cm^2$, 302 nm), the cells were cultured for 30 minutes and 20 µM fluorescent substrate DCF-DA was treated for 30 minutes. The nuclei were stained with DAPI. After washing with PBS, the treated cells were sonicated. The fluorescence intensity of DCF and DAPI was measured at 485 nm/535 nm and 355 nm/460 nm and calculated as a ratio of DCF/DAPI (FIG. 9). The graph in FIG. 9 shows relative values based on UVB(+). The results of statistical analysis (ANOVA with post hoc Tukey) show a significant difference ($p<0.05$) between the different alphabetical letters (a, b, c, d, e, f). The result in FIG. 9 shows that ESG and RG can inhibit ROS accumulation in a concentration-dependent manner, whereas natural glycogen (OG) does not have an ROS accumulation-inhibitory effect.

Figure 10:
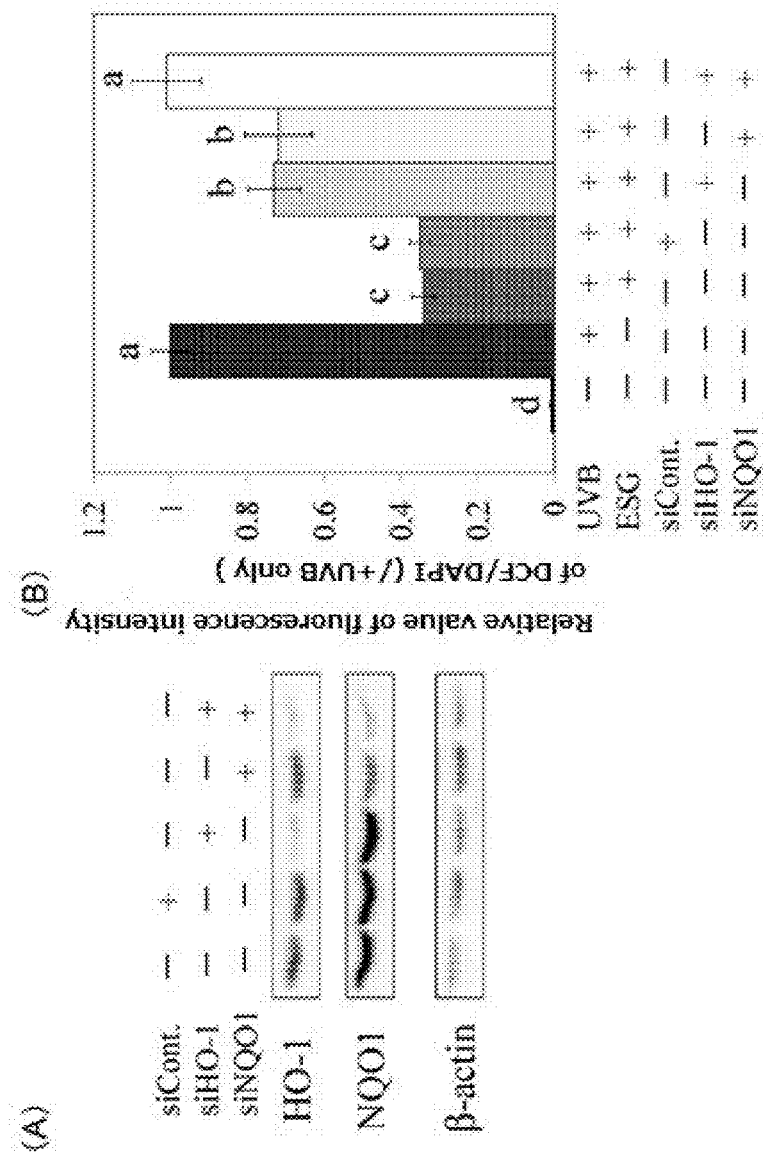
FIG. 10 shows the influence of ESG on ROS accumulation in HO-1 and NQO-1 knockdown NHEK.

Example 10: Influence on ROS Accumulation in HO-1 and NQO-1 Knockdown Cells (FIG. 10)

NHEK was seeded in 35-mm dishes and cultured for 24 hours. Using a transfection reagent (Lipofectamine RNAiMAX), siRNAs targeted to HO-1 and NQO-1 were introduced into the cells to perform RNA interference. The siRNA and RNAiMAX for each of HO-1 and NQO-1 were added and allowed to act for 48 hours.

The RNA-interfered cells were collected and the expression levels of the target proteins were detected by Western blotting (FIG. 10(A)).

ESG in a final concentration of 600 µg/mL was allowed to act on the RNA-interfered cells for 24 hours. After UVB irradiation (20 $mJ/cm^2$, 302 nm), the cells were cultured for 30 minutes and treated with a 20 µM fluorescent substrate DCF-DA for 30 minutes. The nuclei were stained with DAPI. After washing with PBSD, the treated cells were sonicated. The fluorescence intensity of DCF and DAPI was measured at 485 nm/535 nm and 355 nm/460 nm and calculated as a ratio of DCF/DAPI (FIG. 10(B)). The graph in FIG. 10(B) shows relative values based on UVB(+). The results of statistical analysis (ANOVA with post hoc Tukey) show a significant difference ($p<0.05$) between the different alphabetical letters (a, b, c, d). The results in FIG. 10 show that the antioxidative effect of ESG is via inducing the expression of antioxidant proteins, HO-1 and NQO-1.

Figure 11:
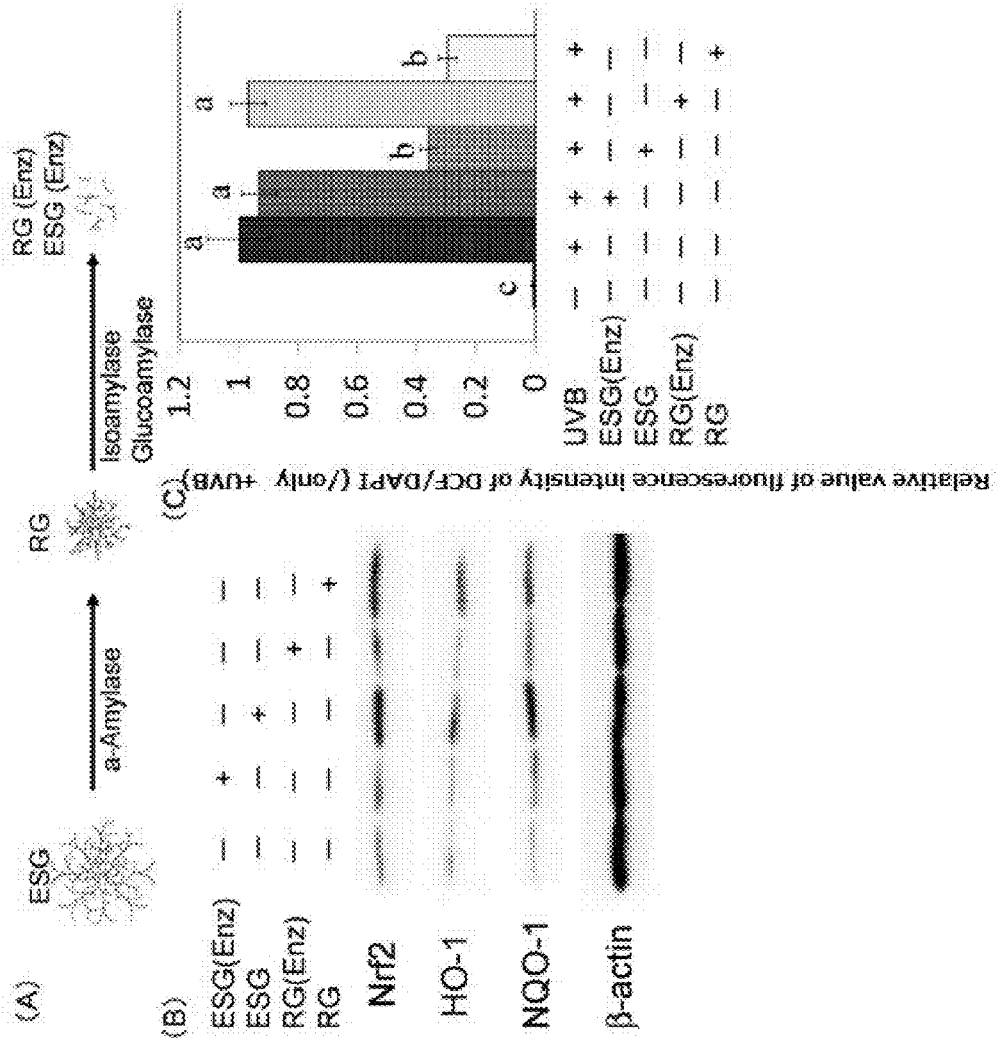
FIG. 11 shows the effects of ESG and RG on the expression levels of antioxidant proteins in NHEK.

Example 11: Effect on the Expression Level of Antioxidant Protein in Macrophage Cells (FIG. 11)

To investigate whether ESG and RG induce an increase in the expression level of an antioxidant protein in a structure-specific manner, RG was digested with isoamylase and glucoamylase into glucose. Analysis of the digested products, ESG (Enz) and RG (Enz), in comparison with RG was performed (FIG. 11(A)).

ESG, RG, ESG (Enz), or RG (Enz) was added to a final concentration of 600 µg/mL to medium in which NHEK was cultured, and each was allowed to act on the cells for 24 hours. The cells were then collected. The expression levels of proteins involved in antioxidative effects were analyzed by Western blotting (FIG. 11(B)).

ESG, RG, ESG (Enz), or RG (Enz) was added to a final concentration of 600 µg/mL to medium in which NHEK was cultured, and each was allowed to act for 24 hours. After UVB irradiation (20 $mJ/cm^2$, 302 nm), the cells were cultured for 30 minutes and treated with a 20 µM fluorescent substrate DCF-DA for 30 minutes. The nuclei were stained with DAPI. After washing with PBS, the treated cells were sonicated. The fluorescence intensity of DCF and DAPI was measured at 485 nm/535 nm and 355 nm/460 nm and calculated as a ratio of DCF/DAPI (FIG. 11(C)). The graph in FIG. 11(C) shows relative values based on UVB(+). The results of statistical analysis (ANOVA with post hoc Tukey) show a significant difference ($p<0.05$) between the different alphabetical letters (a, b, c). The results show that branched ESG and RG have an antioxidant protein expression-enhancing effect, whereas RG (Enz) and ESG (Enz) obtained by enzymatic degradation into glucose have no such effect.

Figure 12:
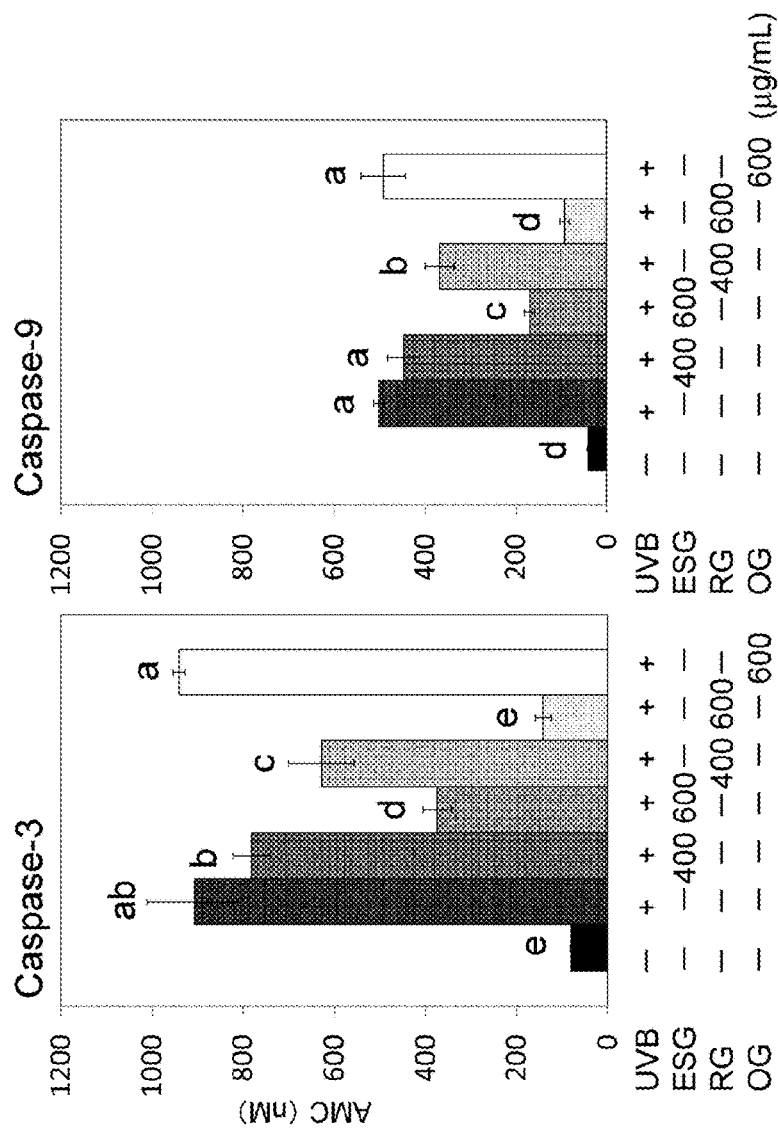
FIG. 12 shows the influence of ESG and RG on UVB irradiation-induced caspase-3 activity and caspase-9 activity in NHEK.

Example 12: Influence on UVB Irradiation-Induced Caspase-3 and Caspase-9 Activity (FIG. 12)

NHEK was seeded in 35-mm dishes. ESG, RG, and OG were added to a final concentration of 400 or 600 µg/mL, and were each allowed to act on the cells for 24 hours. After UVB irradiation (20 $mJ/cm^2$, 302 nm), the cells were cultured for 24 hours and then collected. Fluorescent substrates, Ac-DMQD-7-amino-4-methylcoumarin (AMC, caspase-3) and Ac-LEHD-ANC (caspase-9), were added to a final concentration of 50 µM to the cell extract and allowed to react at 37° C. for 1 hour. The fluorescence intensity of AMC was measured at 355 nm/460 nm (FIG. 12). The graph shows the AMC amount calculated from a calibration curve. The results of statistical analysis (ANOVA with post hoc Tukey) show a significant difference ($p<0.05$) between the different alphabetical letters (a, ab, b, c, d, e). The results in FIG. 12 show that ESG and RG suppress the amounts of caspase-3 and caspase-9 in a dose-dependent manner and can inhibit apoptosis due to UVB irradiation.

The invention claimed is:

1. A method of promoting antioxidant enzyme production in a mammal comprising administering an enzymatically synthesized glycogen (ESG) or an α-amylase digest thereof (RG) to the mammal, thereby promoting antioxidant enzyme production in the mammal, which is determined by measuring the level of the antioxidant enzyme.

2. The method according to claim 1, wherein the antioxidant enzyme is hemeoxygenase 1 (HO-1).

3. The method according to claim 1, wherein the antioxidant enzyme is NAD(P)H quinone oxidoreductase 1 (NQO-1).

4. The production method according to claim 1, wherein the production of the antioxidant enzyme is promoted by increasing the expression of NF-E2 related factor 2 (Nrf-2).

5. A method of treating gastrointestinal tract inflammation in a mammal in need thereof comprising administering an enzymatically synthesized glycogen (ESG) or an α-amylase digest thereof (RG) to the mammal, thereby treating gastrointestinal tract inflammation in the mammal by promoting antioxidant enzyme production, which is determined by measuring the level of the antioxidant enzyme.

6. A method comprising adding an enzymatically synthesized glycogen (ESG) or an α-amylase digest thereof (RG) to an antioxidant food or beverage composition, thereby producing an antioxidant food or beverage to promote antioxidant enzyme production, which is determined by measuring the level of the antioxidant enzyme.

7. The method according to claim 2, wherein the production of the antioxidant enzyme is promoted by increasing the expression of NF-E2 related factor 2 (Nrf-2).

8. The method according to claim 3, wherein the production of the antioxidant enzyme is promoted by increasing the expression of NF-E2 related factor 2 (Nrf-2).

9. A method comprising adding an enzymatically synthesized glycogen (ESG) or an α-amylase digest thereof (RG) to an antioxidant, a reactive oxygen species (ROS) inhibitor, an antioxidant cosmetic, or a UV care cosmetic to promote antioxidant enzyme production, which is determined by measuring the level of the antioxidant enzyme composition, thereby producing an antioxidant, an ROS inhibitor, an antioxidant cosmetic, or a UV care cosmetic.

10. The method according to claim 9, wherein an antioxidant is produced.

11. The method according to claim 9, wherein an ROS inhibitor is produced.

12. The method according to claim 9, wherein an antioxidant cosmetic is produced.

13. The method according to claim 12, wherein the antioxidant cosmetic exerts an antioxidative effect by promoting the production of an antioxidant enzyme.

14. The method according to claim 9, wherein a UV care cosmetic is produced.

* * * * *